United States Patent
Baker, Jr. et al.

(10) Patent No.: US 9,301,697 B2
(45) Date of Patent: Apr. 5, 2016

(54) SYSTEMS AND METHODS FOR RECALIBRATING A NON-INVASIVE BLOOD PRESSURE MONITOR

(75) Inventors: Clark R. Baker, Jr., Newman, CA (US); James Nicholas Watson, Dunfermline (GB); Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1666 days.

(21) Appl. No.: 12/242,858

(22) Filed: Sep. 30, 2008

(65) Prior Publication Data

US 2010/0081944 A1 Apr. 1, 2010

(51) Int. Cl.
| | |
|---|---|
| A61B 5/02 | (2006.01) |
| A61B 5/021 | (2006.01) |
| A61B 5/022 | (2006.01) |
| G06F 19/00 | (2011.01) |
| A61B 5/1455 | (2006.01) |
| A61B 5/00 | (2006.01) |

(52) U.S. Cl.
CPC .......... *A61B 5/021* (2013.01); *A61B 5/022* (2013.01); *A61B 5/02125* (2013.01); *A61B 5/02225* (2013.01); *A61B 5/1455* (2013.01); *A61B 5/7239* (2013.01); *A61B 2560/0223* (2013.01); *G06F 19/3406* (2013.01); *G06F 19/3412* (2013.01); *G06F 19/3487* (2013.01)

(58) Field of Classification Search
None
See application file for complete search history.

(56) References Cited

U.S. PATENT DOCUMENTS

| | | | |
|---|---|---|---|
| 3,835,840 | A | 9/1974 | Mount |
| 4,561,447 | A | 12/1985 | Kawamura et al. |
| 4,676,253 | A | 6/1987 | Newman |
| 4,714,080 | A | 12/1987 | Edgar et al. |
| 4,729,382 | A | 3/1988 | Schaffer |
| 4,830,017 | A | 5/1989 | Perry |
| 4,836,213 | A | 6/1989 | Wenzel et al. |
| 4,854,327 | A | 8/1989 | Kunig |
| 4,898,176 | A | 2/1990 | Petre |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — Russell S Negin
(74) *Attorney, Agent, or Firm* — Shvarts & Leiz LLP (57) ABSTRACT

Techniques for non-invasive blood pressure monitoring are disclosed. Data corresponding to a patient may be received from a hospital information system. The data may include, for example, drug administration data, medical procedure data, medical equipment data, or a combination thereof. Whether a blood pressure monitoring system needs to be recalibrated may be determined, based at least in part on the received data. If it is determined that the blood pressure monitoring system needs to be recalibrated, the recalibration may be performed and at least one blood pressure measurement of the patient may be computed using the recalibrated blood pressure monitoring system.

22 Claims, 5 Drawing Sheets

(56) References Cited

U.S. PATENT DOCUMENTS

| | | |
|---|---|---|
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,365,066 A | 11/1994 | Krueger et al. |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu et al. |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz et al. |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,310 B1 | 10/2002 | Swedlow et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,510 B2 | 8/2003 | Swedlow et al. |
| 6,606,511 B1 | 8/2003 | Ali et al. |
| 6,616,613 B1 | 9/2003 | Goodman |
| 6,618,602 B2 | 9/2003 | Levin |
| 6,626,839 B2 | 9/2003 | Doten et al. |
| 6,631,281 B1 | 10/2003 | Kastle |
| 6,643,531 B1 | 11/2003 | Katarow |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,192,403 B2 * | 3/2007 | Russell .................... 600/504 |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |

(56) References Cited

U.S. PATENT DOCUMENTS

| | | |
|---|---|---|
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,430,444 B2 | 9/2008 | Pologe et al. |
| 7,455,643 B1 | 11/2008 | Li et al. |
| 7,481,772 B2 | 1/2009 | Banet |
| 7,485,095 B2 | 2/2009 | Shusterman |
| 2003/0135124 A1 | 7/2003 | Russell |
| 2003/0167012 A1 | 9/2003 | Friedman |
| 2004/0006261 A1 | 1/2004 | Swedlow et al. |
| 2004/0073121 A1 | 4/2004 | Sun |
| 2005/0148885 A1 | 7/2005 | Tweed et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0253016 A1 | 11/2006 | Baker et al. |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0249467 A1 | 10/2007 | Hong et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0132798 A1 | 6/2008 | Hong et al. |
| 2008/0214903 A1 | 9/2008 | Orbach |
| 2008/0214942 A1 | 9/2008 | Oh et al. |
| 2008/0221410 A1 | 9/2008 | Campbell et al. |
| 2008/0242955 A1 | 10/2008 | Uutela et al. |
| 2009/0048497 A1 | 2/2009 | Keren |

FOREIGN PATENT DOCUMENTS

| | | |
|---|---|---|
| EP | 0793942 | 9/1997 |
| EP | 1782728 A1 | 5/2007 |
| GB | 2 356 250 | 5/2001 |
| GB | 2 356 251 | 5/2001 |
| GB | 2 356 252 | 5/2001 |
| JP | 03-231630 | 10/1991 |
| JP | 6142082 A | 5/1994 |
| JP | 07-136136 | 5/1995 |
| JP | 03-225268 A1 | 12/2003 |
| JP | 24113353 | 4/2004 |
| JP | 27330708 A2 | 12/2007 |

OTHER PUBLICATIONS

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

International Search Report PCT/IB2009/006893, 4 pages, mailed Jan. 19, 2010.

Berne, Robert M., Levy, Matthew N., eds., Physiology, 2nd edition, St. Louis, Mosby, 1988, pp. 357-681.

Moyle, John TB, Hahn, CEW, Adams, Anthony P, Pulse Oximetry, Revised Edition, London, BMJ, 1998.

\* cited by examiner

SYSTEMS AND METHODS FOR RECALIBRATING A NON-INVASIVE BLOOD PRESSURE MONITOR

SUMMARY

The present disclosure relates to blood pressure monitoring and, more particularly, the present disclosure relates to systems and methods for recalibrating a non-invasive blood pressure monitor.

In some embodiments, a patient's blood pressure may be measured using a continuous non-invasive blood pressure (CNIBP) monitoring system, which may include at least one pulse oximeter. An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

Multiple PPG signals may be detected using probes or sensors positioned at different points in a patient's body. For example, a first probe or sensor may be attached to the patient's ear while a second probe or sensor may be attached to the patient's finger or toe. A differential pulse transit time (DPTT) may be measured between PPG signals that can be used to compute blood pressure measurements on a continuous or periodic basis. Chen et al U.S. Pat. No. 6,599,251, issued Jul. 29, 2003, which is hereby incorporated by reference herein in its entirety, discloses some techniques for continuous and non-invasive blood pressure monitoring using two probes or sensors that may be used in conjunction with the present disclosure.

In some embodiments, blood pressure may be computed with the use of only a single sensor or probe. In such scenarios, a time between two characteristic points of a PPG signal detected by the single sensor or probe may be measured and used in place of a DPTT to compute a patient's blood pressure. Characteristic points may be, for example, turning points in the 1st, 2nd, 3rd, or other derivative of a PPG signal. Further details on using a single probe or sensor to compute blood pressure are described in commonly assigned U.S. patent application Ser. No. 12/242,238, entitled "Systems and Methods for Non-Invasive Blood Pressure Monitoring", filed on Sep. 30, 2008, which is hereby incorporated by reference herein in its entirety.

In other embodiments, blood pressure may be computed based on the area under at least a portion of a detected PPG signal. Techniques for using area measurements to compute blood pressure are provided in commonly assigned U.S. patent application Ser. No. 12/242,867, now U.S. Pat. No. 8,398,556, entitled "Systems and Methods for Non-Invasive Blood Pressure Determination", filed on Sep. 30, 2008, which is hereby incorporated by reference herein in its entirety.

The DPTT and area measurements may vary not only with a patient's blood pressure, but also with the patient's arterial compliance (vasotone), which in turn may vary in response to a variety of factors. In order to account for the effect of the patient's vasotone in computing blood pressure measurements, a CNIBP measuring system may perform an initial calibration using a reference blood pressure measurement (e.g., using a cuff wrapped around a patient's arm). This initial calibration may be used to set values for constants or parameters in one or more equations relating the DPTT to a desired blood pressure measurement. After initial calibration is performed, recalibration of the CNIBP system may be required periodically (e.g., every 30 minutes or any other suitable interval) or in response to events that may indicate a change to the vasotone of the arteries connecting the patient's heart to any of the sensor sites. For example, events that may indicate a need for a recalibration may include administration of certain drugs (e.g., vasoactive drugs such as anesthetics), certain surgical procedures or steps that may cause pain or otherwise aggravate the patient, or changes in the elevation of the sensor sites relative to the blood pressure cuff.

CNIBP systems may determine that the system needs to be recalibrated in several ways. One way to determine such a need is through the use of indirect data. For instance, the system may detect certain changes in the computed blood pressure (e.g., measurements falling outside of a pre-determined range or deviating a certain amount from a running average) or variations in the shape of measured PPG waveforms (e.g., as measured by the rise-to-fall time of the waveform or the relative amplitude of the dicrotic notch) that indicate that a recalibration is needed. However, relying solely or primarily on indirect recalibration events may have several drawbacks. For example, a significant amount of time may elapse between the occurrence of a change in vasotone and the detection of that change, which may cause inaccuracies in CNIBP measurements and may, in certain cases, trigger false CNIBP alarms. Additionally, the detection of indirect recalibration events may require unnecessary cuff inflations, which may interrupt the CNIBP measurements, and disturb the patient unnecessarily (e.g., by awakening a sleeping patient).

In some embodiments, a CNIBP measuring system may be recalibrated in response to direct events instead of, or in addition to, indirect events indicating a detected or expected change in vasotone. As an example, a direct event may reflect patient data stored in a hospital information system that contains real-time information about the patient. Such data may include, for instance, manual entries of drug administration or other procedures. The data may be automatically generated (e.g., by scanning a drug vial using a barcode or radio-frequency identification reader to determine the identity of a drug and when it will be administered to a patient, or by storing data from surgical equipment such as cutting and pounding devices). Such data may be updated in real-time, in appropriate intervals, or a combination thereof. As another example, the CNIBP measuring system may detect changes in the elevation of one or more sensors that may require recalibration. Techniques for determining such changes in elevation are disclosed in pending Baker, Jr. et al. U.S. Publication No. US 2006/0253016, filed Nov. 18, 2005, which is hereby incorporated by reference herein in its entirety. A CNIBP measuring system may rely on indirect recalibration events, direct recalibration events, or a suitable combination thereof. In some embodiments, the system may be manually configured to use a certain subset of available indirect and direct events.

A recalibration event may automatically trigger a recalibration sequence. Recalibration may be performed, in some embodiments, by measuring a patient's blood pressure (or a reference blood pressure) and then measuring the corresponding elapsed time between PPG signals or within a single PPG signal, or area under a PPG signal, detected using appropriately placed sensors or probes. Updated or refined values for one or more constants or parameters used in the blood pressure measurement determination may then be computed based at least in part on the recalibration. These updated or refined constant or parameter values may then be used to determine the patient's blood pressure until the next recalibration sequence is performed (or for some predetermined length of time).

In some embodiments, a direct recalibration event may indicate when the desired recalibration should be performed. For instance, the time required for a drug to take effect may vary based on factors such as the type of drug in question, the drug's mode of action, and how the drug is delivered. Therefore, the CNIBP measuring system may schedule recalibration based on such factors. As an example, recalibration may be scheduled for a time when the drug's effect on the patient is nearly complete. As another example, recalibration may be scheduled to occur several times at preset intervals (e.g., for drugs that are expected to exert a significant but prolonged effect on a patient's vasotone).

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Some CNIBP monitoring techniques may utilize two probes or sensors positioned at two different locations on a subject's body. The elapsed time, T, between the arrivals of corresponding points of a pulse signal at the two locations may then be determined using signals obtained by the two probes or sensors. The estimated blood pressure p, may then be related to the elapsed time, T, by $$p = a + b \cdot \ln(T) \quad (1)$$

where a and b are constants that may be dependent upon the nature of the subject and the nature of the signal detecting devices. Other suitable equations using an elapsed time between corresponding points of a pulse signal may also be used to derive an estimated blood pressure measurement. In some embodiments, a single probe or sensor may be used, in which case the variable T in equation (1) would represent the time between two characteristic points within a single detected PPG signal. In still other embodiments, the area under at least part of a detected PPG signal may be used to compute blood pressure instead of time.

The values of constants a and b may be determined by way of an initial calibration that uses a reference blood pressure measurement taken from the patient (e.g., using a blood pressure cuff). These constants may be adjusted during blood pressure measurement periodically or in response to recalibration events. As discussed in more detail below, according to some embodiments, recalibration events may be based at least in part on indirect data, direct data, any other suitable factor (e.g., a manual request for recalibration), or any suitable combination thereof. Indirect data may include, for example, blood pressure measurements or characteristics of PPG waveforms. Direct data may include, for example, drug administration data, medical procedure data, medical equipment data, other data received from a hospital information system, data indicative of the elevation of either or both PPG probes or sensors, or any suitable combination thereof. In some embodiments, direct recalibration data may include information that facilitates proper scheduling of system recalibration.

Figure 1:
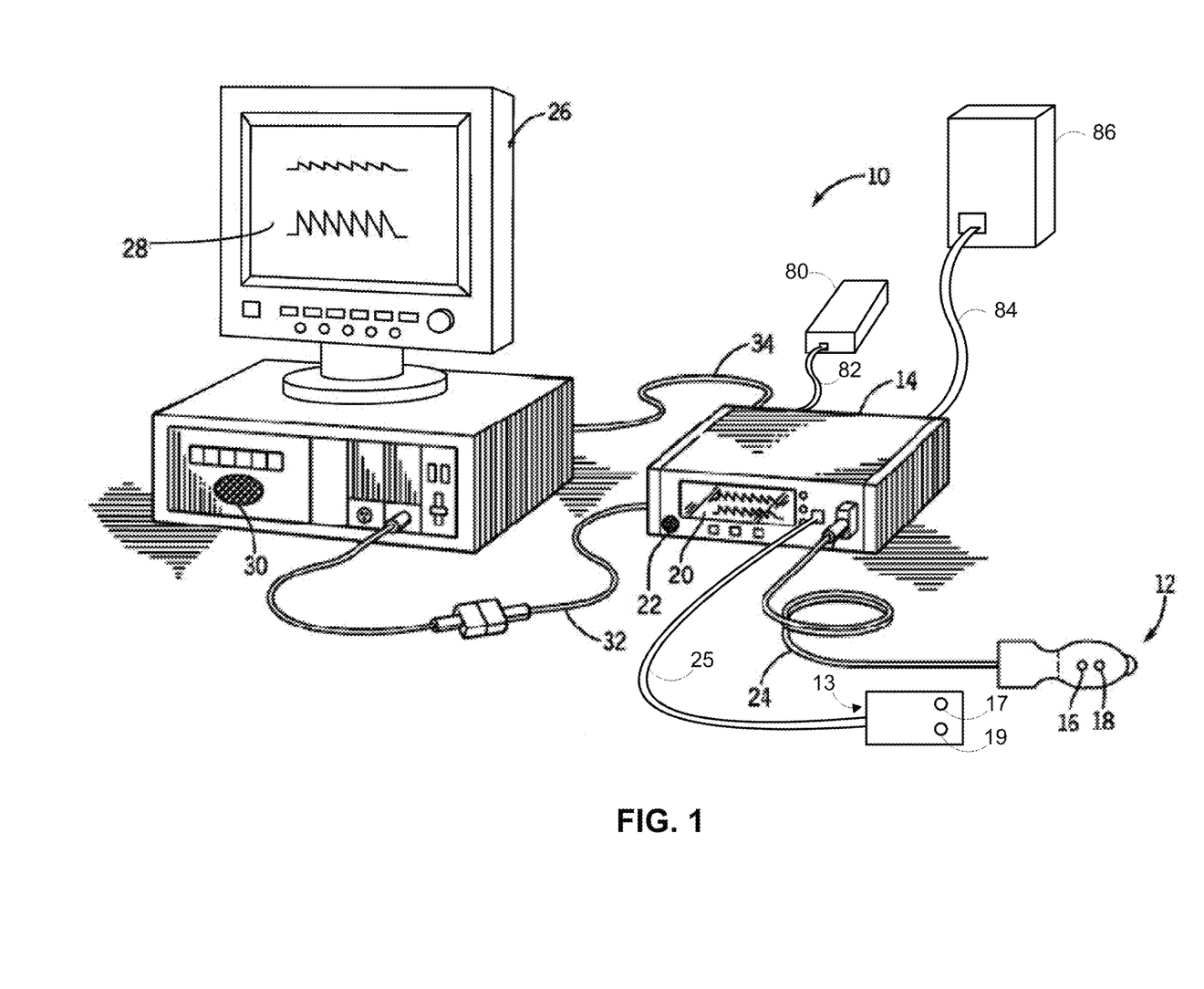
FIG. 1 shows an illustrative CNIBP monitoring system in accordance with some embodiments.

FIG. 1 is a perspective view of an embodiment of a CNIBP monitoring system 10 that may also be used to perform pulse oximetry. System 10 may include sensors 12 and 13 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue. Similarly, sensor 13 may include an emitter 17 and a detector 19, which may operate in a fashion similar to that of emitter 16 and detector 18, respectively Sensors 12 and 13 may be attached to different locations of a patient's body in order to measure values for time T in equation (1) above and thereby facilitate measurement of the patient's blood pressure. As an example, sensor 12 may be attached to the patient's finger, while sensor 13 may be attached to the patient's ear. It will be appreciated that other sensor locations may be used, as appropriate, and in some embodiments, only a single sensor or probe may be used.

According to an embodiment, emitter 16 and detector 18 may be on opposite sides of a digit such as a finger or toe, in which case the light that is emanating from the tissue has passed completely through the digit. In an embodiment detector 18 (e.g., a reflective sensor) may be positioned anywhere a strong pulsatile flow may be detected (e.g., over arteries in the neck, wrist, thigh, ankle, ear, or any other suitable location). In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

Similarly, according to an embodiment, emitter 17 and 19 may be on opposite sides of an ear (e.g., positioned on opposite sides of a patient's earlobe). In an embodiment, emitter 17 and detector 19 may be arranged so that light from emitter 17 penetrates the tissue and is reflected by the tissue into detector 19, such as a sensor designed to obtain pulse oximetry or CNIBP data from a patient's forehead.

According to another embodiment system 10 may include a plurality of sensors forming a sensor array in lieu of either or both of sensors 12 and 13. Each of the sensors of the sensor array may be a complementary metal oxide semiconductor (CMOS) sensor. Alternatively, each sensor of the array may be charged coupled device (CCD) sensor. In another embodiment, the sensor array may be made tip of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

In an embodiment, the sensors or sensor array may be connected to and draw its power from monitor 14 as shown. In another embodiment, the sensors may be wirelessly connected to monitor 14 and may each include its own battery or similar power supply (not shown). Monitor 14 may be configured to calculate physiological parameters (e.g., blood pressure) based at least in part on data received from sensors 12 and 13 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensors 12 and 13 may be communicatively coupled to monitor 14 via cables 24 and 25, respectively. However, in other embodiments, a wireless transmission device (not shown) or the like may be used instead of or in addition to either or both of cables 24 and 25.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a patient, or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. In still other embodiments, calibration device 80 is completely integrated within monitor 14.

Recalibration of monitor 14 may be triggered at any suitable times. For example, monitor 14 may be configured to perform recalibration on a periodic basis (e.g., once every 30 minutes or any other appropriate time interval). Monitor 14 may also perform recalibration in response to indirect recalibration triggers. For example, monitor 14 may receive blood pressure measurements, amplitude measurements of PPG waveforms, any other suitable information, or any suitable combination thereof and determine that recalibration is necessary in response to certain changes in such measurements.

In some embodiments, monitor 14 may alternatively or additionally initiate recalibration in response to indirect recalibration triggers. Such triggers may be based at least in part on data received from hospital information system 86, which may be coupled to monitor 14 through cable 84, through a wired network (not shown), wirelessly, or through any other suitable means. Hospital information system 86 may include a central or distributed database, data input and output terminals, primary and backup storage, or any other suitable components. Hospital information system 86 may be adapted to store patient data and transmit this data to monitor 14 in order to facilitate the making of recalibration decisions. For example, hospital information system 86 may store and transmit data relating to actual or anticipated drug administrations or medical procedures for a patient that could affect a patient's vasotone and therefore require recalibration. Such data may include the identity of the drug or procedure, the actual or expected start and end time of the administration or procedure, drug dosage, method of drug action and delivery, any other suitable information, or any suitable combination thereof. In some embodiments, the data may be used by monitor 14 in order to schedule one or more recalibrations. For instance, it may be desirable for a recalibration to occur when a drug has mostly or completely taken effect. As another example, drugs that have relatively significant but relatively gradual effects on vasotone may require several recalibrations.

In some embodiments, monitor 14 may, additionally or alternatively, receive and utilize direct recalibration events from sources other than hospital information system 86. For example, either or both of sensors 12 and 13 may transmit information about their position (e.g., elevation relative to a blood pressure cuff) to monitor 14. Monitor 14 may then use this direct data to trigger a recalibration when the elevation of either or both of sensors 12 and 13 changes more than a certain amount, as measured relative to a pre-defined threshold, a moving average, or any other suitable metric. It will be appreciated that other types of direct information and other information sources may be used, and the disclosure is not limited in this respect.

Figure 2:
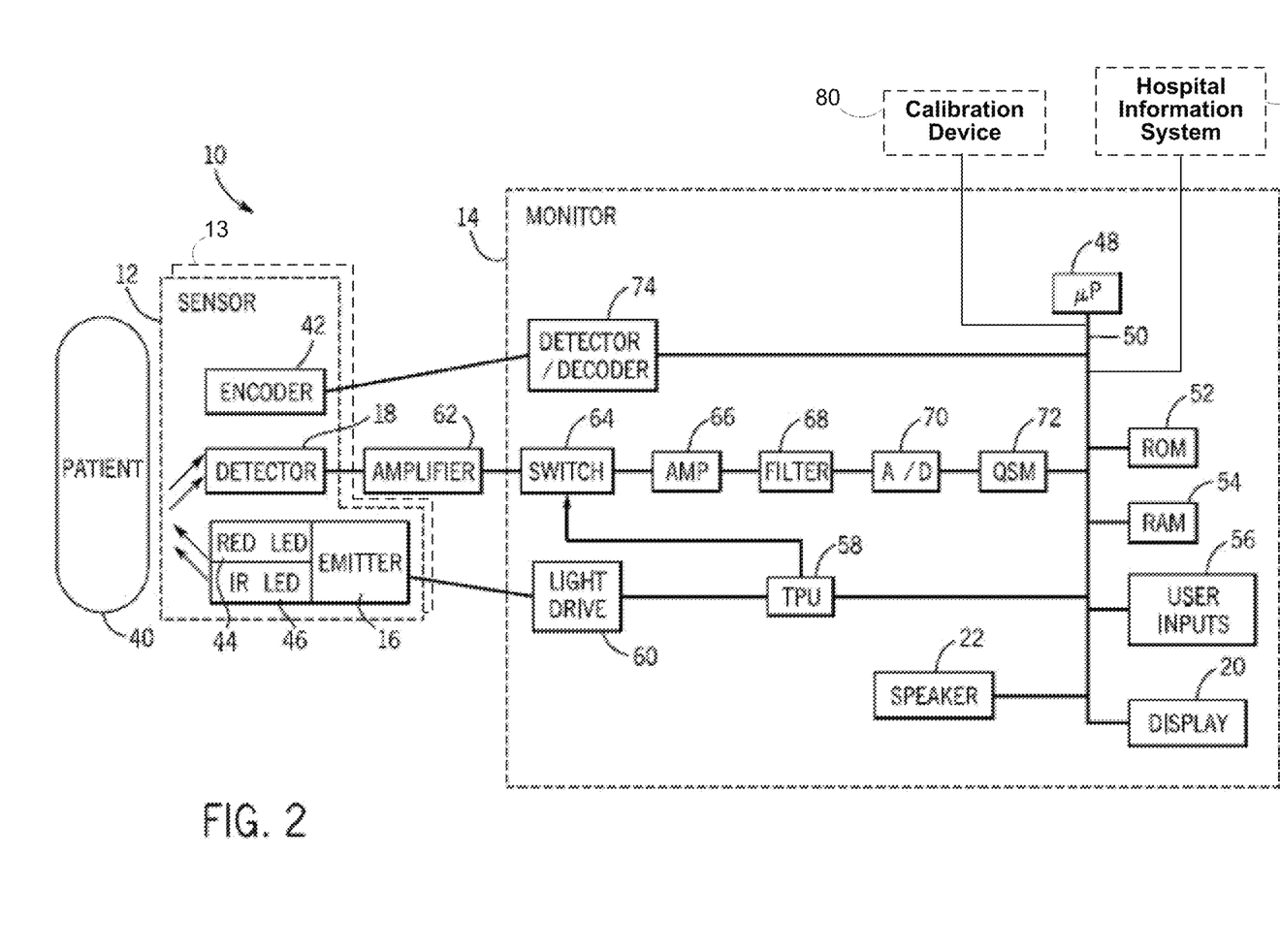
FIG. 2 is a block diagram of the illustrative CNIBP monitoring system of FIG. 1 coupled to a patient in accordance with some embodiments.

FIG. 2 is a block diagram of a CNIBP monitoring system, such as system 10 of FIG. 1, which may be coupled to a patient 40 in accordance with an embodiment. Certain illustrative components of sensors 12 and 13 and monitor 14 are illustrated in FIG. 2. Because sensors 12 and 13 may include similar components and functionality, only sensor 12 will be discussed in detail for ease of illustration. It will be understood that any of the concepts, components, and operation discussed in connection with sensor 12 may be applied to sensor 13 as well (e.g., emitter 16 and detector 18 of sensor 12 may be similar to emitter 17 and detector 19 of sensor 13). Similarly, it will be understood that, as discussed in connection with FIG. 1, certain embodiments may use only a single sensor or probe, instead of a plurality of sensors or probes as illustrated in FIG. 2.

Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

In some embodiments, microprocessor 48 may be operable to receive data relating to detected PPG signals, computed blood pressure measurements, sensor elevation, or any other suitable data for use in determining whether monitor 14 should be recalibrated. For example, microprocessor 48 may receive reference blood pressure measurements from calibration device 80, which may be coupled to microprocessor 48 through bus 50. Additionally, microprocessor 48 may receive patient data from hospital information system 86 through bus 50 that may indicate a need for recalibration, such as data relating to expected drug administrations, medical procedures, or medical equipment.

Upon receiving data from calibration device 80, hospital information system 86, or any other suitable source, microprocessor 48 may decide whether a recalibration is appropriate and, if so, perform such recalibration. Recalibration may include, for example, computing values for constants or parameters of equations used in determining a patient's blood pressure using the received data, then transmitting the computed constants or parameters to ROM 52, RAM 54, or both for storage.

Figure 3:
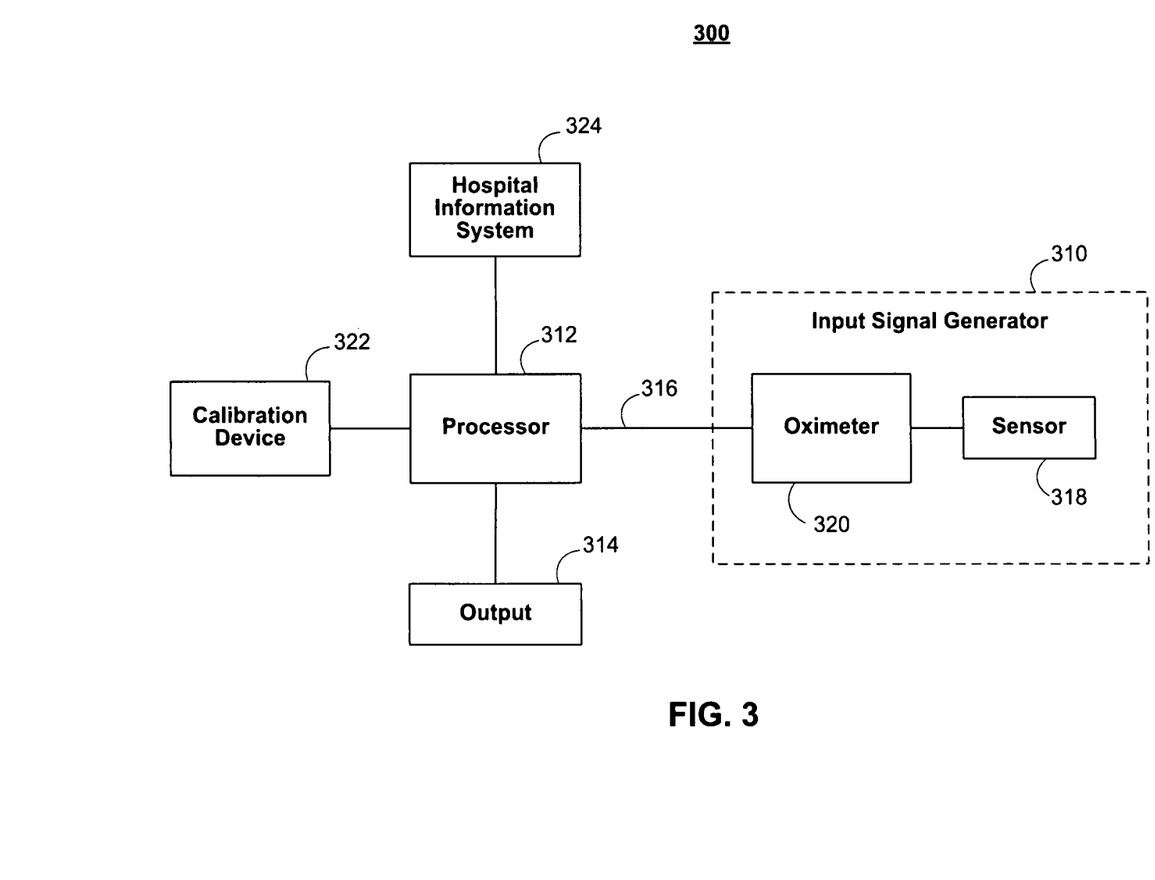
FIG. 3 is a block diagram of an illustrative signal processing system in accordance with some embodiments.

FIG. 3 is an illustrative processing system 300 in accordance with an embodiment. In this embodiment, input signal generator 310 generates an input signal 316. As illustrated, input signal generator 310 may include oximeter 320 (or similar device) coupled to sensor 318, which may provide as input signal 316 a PPG signal. It will be understood that input signal generator 310 may include any suitable signal source, signal generating data, signal generating equipment, or any combination thereof to produce signal 316. Additionally, input signal generator 310 may in some embodiments include more than one sensor 318.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may determine the time difference, T, between any two chosen characteristic points of a PPG signal obtained from input signal generator 310. As another example, if input signal generator contains more than one sensor 318, processor 312 may determine the time difference, T, required for a PPG signal to travel from one sensor 318 to another. Processor 312 may also be configured to apply equation (1) (or any other blood pressure equation using an elapsed time value) and compute estimated blood pressure measurements on a continuous or periodic basis. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to calibration device 322 that may generate or receive as input reference blood pressure measurements for use in calibrating CNIBP calculations. Processor 312 may additionally be coupled to hospital information system 324, which may store and transmit direct information indicative of a need for recalibration, such as information relating to scheduled drug administrations, medical procedures, medical equipment, or any suitable combination thereof. Processor 312 may perform initial calibration, recalibration, or both of the CNIBP measuring system, using information received from input signal generator 310, calibration device 322, hospital information system 324, or any other suitable device.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous blood pressure monitoring solution.

According to the present disclosure, reliable blood pressure measurements may be derived substantially continuously from PPG signals by recalibrating parts of the CNIBP system in response to direct recalibration events, indirect recalibration events, or both. These direct and indirect recalibration events may be detected and triggered from any suitable source, as discussed above, including a hospital information system, one or more sensors or probes attached to a patient's body, or one or more processors or memories that output data derived from the sensors or probes. The present disclosure may be applied to measuring systolic blood pressure, diastolic blood pressure, or both systolic and diastolic blood pressure on an on-going, continuous, or periodic basis.

According to the present disclosure, reliable blood pressure measurements may be derived from a PPG signal obtained from a single sensor or probe, or from multiple PPG signals obtained from multiple sensors or probes. In some embodiments, the constants a and b in equation (1) above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

In some embodiments, the calibration may include performing calculations mathematically equivalent to $$a = c_1 + \frac{c_2(P_0 - c_1)}{\ln(T_0) + c_2} \quad (2)$$

and $$b = \frac{P_0 - c_1}{\ln(T_0) + c_2} \quad (3)$$

to obtain values for the constants a and b, where $c_1$ and $c_2$ are predetermined constants that may be determined, for example, based on empirical data.

In other embodiments, determining the plurality of constant parameters in the multi-parameter equation (1) may include performing calculations mathematically equivalent to $$a = P_0 - (c_3 T_0 + c_4)\ln(T_0) \quad (4)$$

and $$b = c_3 T_0 + c_4 \quad (5)$$

where a and b are first and second parameters and $c_3$ and $c_4$ are predetermined constants that may be determined, for example, based on empirical data.

In some embodiments, the multi-parameter equation (1) may include a non-linear function which is monotonically decreasing and concave upward in a manner specified by the constant parameters.

Figure 4:
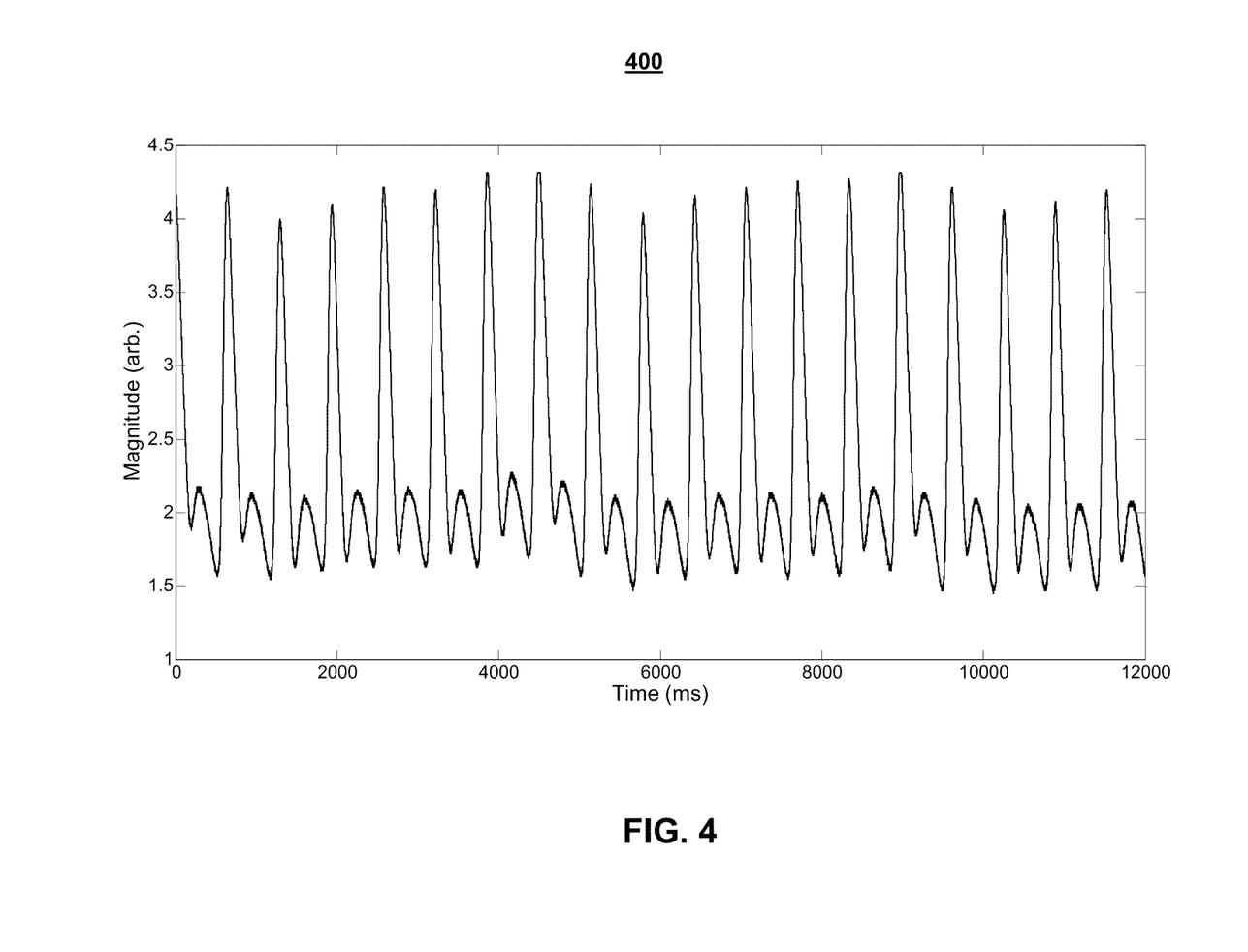
FIG. 4 shows an illustrative PPG signal in accordance with some embodiments.

FIG. 4 shows illustrative PPG signal 400. As described above, in some embodiments PPG signal 400 may be generated by a pulse oximeter or similar device positioned at any suitable location of a subject's body. Additionally, PPG signal 400 may be generated at each of a plurality of locations of a subject's body, with at least one probe or sensor attached to each location. The time T that it takes for PPG signal 400 to travel from one location to another location (e.g., from a patient's ear to the patient's finger or toe) may then be measured and used to derive a blood pressure measurement for the patient using a calibrated version of equation (1) or using any other relationship, such as lookup tables and the like. Time T may be measured, for example, by determining the difference between how long it takes for a given characteristic point, observed in the PPG signal at the first sensor or probe location, to appear in the PPG signal at the second sensor or probe location.

In some embodiments, PPG signal 400 may be generated using only a single sensor or probe attached to the subject's body. In such a scenario, the time difference, T, may correspond to the time it takes the pulse wave to travel a predetermined distance (e.g., a distance from the sensor or probe to a reflection point and back to the sensor or probe). Characteristic points in the PPG signal may include the time between various peaks in the PPG signal and/or in some derivative of the PPG signal. For example, in some embodiments, the time difference, T, may be calculated between (1) the maximum peak of the PPG signal in the time domain and the second peak in the 2nd derivative of the PPG signal (the first 2nd derivative peak may be close to the maximum peak in the time domain) and/or (2) peaks in the 2nd derivative of the PPG signal. Any other suitable time difference between any suitable characteristic points in the PPG signal (e.g., PPG signal 400) or any derivative of the PPG signal may be used as T in other embodiments.

In some embodiments, the time difference between the adjacent peaks in the PPG signal, the time difference between the adjacent valleys in the PPG signal, or the time difference between any combination of peaks and valleys, can be used as the time difference T. As such, adjacent peaks and/or adjacent valleys in the PPG signal (or in any derivative thereof) may also be considered characteristic points. In some embodiments, these time differences may be divided by the actual or estimated heart rate to normalize the time differences. In some embodiments, the resulting time difference values between two peaks may be used to determine the systolic blood pressure, and the resulting time difference values between two valleys may be used to determine the diastolic blood pressure.

Characteristic points in a PPG signal (e.g., PPG signal 400) may be identified in a number of ways. For example, in some embodiments, the turning points of 1st, 2nd, 3rd (or any other) derivative of the PPG signal are used as characteristic points. Additionally or alternatively, points of inflection in the PPG signal (or any suitable derivative thereof) may also be used as characteristic points of the PPG signal.

In some embodiments, blood pressure may be determined by, for example, measuring the area under a pulse or a portion of the pulse in the PPG signal (e.g., PPG signal 400). These measurements may be correlated with empirical blood pressure data (corresponding to previous blood pressure measurements of the patient or one or more other patients) to determine the blood pressure. In some implementations, the blood pressure may be determined by looking up the area measurement values in a table, which may be stored in a memory, to obtain corresponding blood pressures. Alternatively, the blood pressure may be determined by using any suitable blood pressure-area mapping equation which is generated based on blood pressure and area measurements associated with one or more patients. For example, measured samples may be plotted in a graph that maps blood pressure to area. The graph may be analyzed to generate a linear-best-fit-line approximation, non-linear best fit line approximation or other suitable approximation from which to derive an equation that may be used to determine blood pressure by providing an area measurement.

Figure 5:
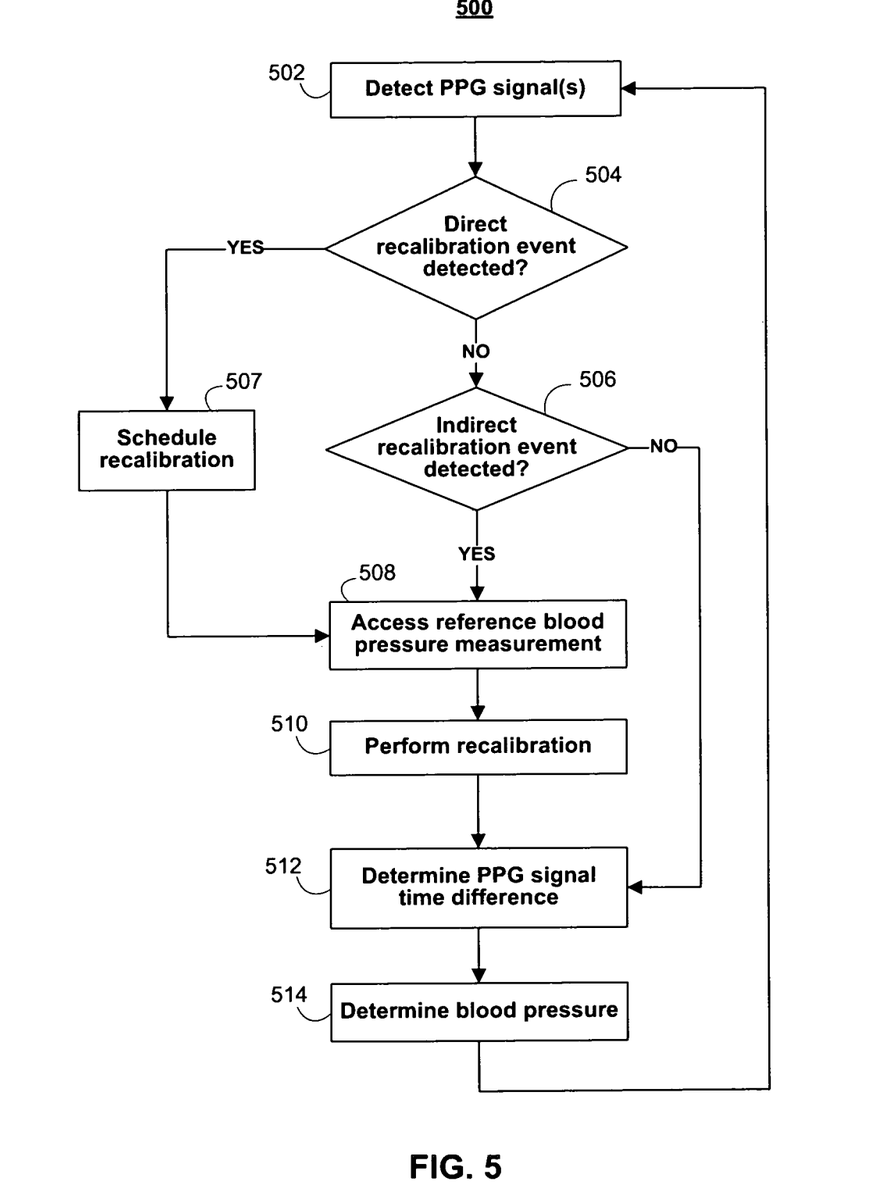
FIG. 5 shows an illustrative process for measuring blood pressure in accordance with some embodiments.

FIG. 5 shows illustrative process 500 for determining blood pressure. At step 502, one or more PPG signals may be detected from a patient. For example, monitor 14 (FIGS. 1 and 2) may be used to detect one or more PPG signals from patient 40 (FIG. 2) using either or both of sensors 12 and 13 (FIGS. 1 and 2).

At step 504, in accordance with some embodiments, it may be determined whether a direct recalibration event has been detected. This determination may be performed in monitor 14 (FIGS. 1 and 2), in calibration device 80 (FIGS. 1 and 2), or in some combination thereof. For example, monitor 14 (FIGS. 1 and 2) may detect a direct recalibration event in response to receiving patient data from hospital information system 86 (FIGS. 1 and 2). Such data may include, for instance, manual entries of drug administration, medical procedures, or medical equipment data for the patient in question. The data may, additionally or alternatively, be automatically generated (e.g., by scanning a drug vial using a barcode or radio-frequency identification reader to determine the identity of a drug and when it was or will be administered to a patient, or by storing data from surgical equipment such as cutting and pounding devices). Other suitable data may be used to trigger direct recalibration events, and the present disclosure is not limited in this respect. Such data may be updated in real-time, in appropriate intervals, or a combination thereof. As another example, monitor 14 (FIGS. 1 and 2) may detect changes in the elevation of one or more sensors such as sensors 12 and 13 (FIGS. 1 and 2) (e.g., relative to a blood pressure cuff) that may require recalibration.

If a direct recalibration event is detected at step 504, process 500 may proceed to step 507. At step 507, recalibration may be scheduled based at least in part upon data received in step 504. For instance, if at step 504 it is determined that a certain drug will be administered to a patient at a particular time, monitor 14 (FIGS. 1 and 2) or calibration device 80 (FIGS. 1 and 2) may determine how long the drug will take to complete its effect upon the patient's vasotone. Such timing information may be transferred from hospital information system 86 (FIGS. 1 and 2), accessed from a memory such as ROM 52 or RAM 54 (FIG. 2), computed based on preexisting relationships, or determined in any other suitable manner. Recalibration may then be scheduled for an appropriate time based at least in part on this timing information. For example, recalibration may be scheduled for a time when the drug's effect is nearly complete or has already been completed. As another example, multiple recalibrations may be scheduled if a drug is expected to exert a significant but gradual effect on the patient's vasotone. The scheduling may be based at least in part on the identity of the drug, the drug's rate of administration, how the drug is delivered, any other suitable factors, or any suitable combination thereof. Process 500 may then proceed to step 508.

On the other hand, if a direct recalibration event is not detected at step 504, process 500 may proceed to step 506. At step 506, it may be determined whether an indirect recalibration event has been detected. This determination may be performed in monitor 14 (FIGS. 1 and 2), in calibration device 80 (FIGS. 1 and 2), or in some combination thereof. For example, monitor 14 (FIGS. 1 and 2) may detect blood pressure readings reflecting certain changes (e.g., measurements falling outside of a pre-determined range or a certain amount past a running average) that indicate a need for recalibration. As another example, PPG signals measured by either or both of sensors 12 and 13 (FIGS. 1 and 2) and processed by monitor 14 (FIGS. 1 and 2) may show certain variations (e.g., in the rise-to-fall time of the waveform or the relative amplitude of the dicrotic notch) that may trigger a recalibration. If an indirect recalibration event is not detected at step 506, process 500 may proceed to step 512. Otherwise, process 500 may proceed to step 508.

If recalibration has been signaled, at step 508 one or more reference blood pressure measurements may be accessed. For example, calibration device 80 (FIGS. 1 and 2) may continuously or periodically generate reference blood pressure measurements for use in calibration. These reference blood pressure measurements may be derived from any suitable invasive or non-invasive blood pressure monitoring technique (e.g., using a blood pressure cuff). The measurements may also be accessed from any suitable storage device, or the measurements may be manually inputted by an operator (e.g., if read from an external monitoring or measurement device).

After the reference blood pressure measurement or measurements are accessed, recalibration may be performed at step 510. For example, one or more of constants a and b of equation (1) above may be updated. Constants a and b may be computed using equations (2) and (3), equations (4) and (5), or any other suitable relationships. Additionally, any other suitable constants or parameters (of any other suitable blood pressure equation) may be updated in other embodiments.

At step 512, a PPG signal time difference may be determined. For example, if sensor 13 (FIGS. 1 and 2) is attached to a first location on a patient's body (e.g., an ear) and sensor 12 (FIGS. 1 and 2) is attached to a second location on the patient's body (e.g., a finger or toe), microprocessor 48 in monitor 14 (FIG. 2) may compute the time it takes for a given PPG signal, or at least one characteristic point in the PPG signal, to travel from one sensor to the other. The time difference may be used as time difference T in equation (1), or in any other suitable fashion. The measured time difference may be determined by averaging a series of recorded time differences over a given time period or in any other suitable way. As another example, a time difference between characteristic points of a single PPG signal may be measured instead (e.g., in embodiments using only a single probe or sensor). In still other embodiments, step 512 may be replaced by a step in which an area of at least one portion of a PPG signal is measured.

Finally, at step 514, a blood pressure measurement may be determined based, at least in part, on the time difference determined at step 512. For example, equation (1) above (or any other blood pressure equation using an elapsed time between the arrivals of corresponding points of a pulse signal) may be used to compute estimated blood pressure measurements. In some embodiments, data other than the time difference between PPG signals may be used (e.g., time difference between characteristic points in a single PPG signal or area under at least a portion of a PPG signal), in which case any appropriate relationship may be used to compute blood pressure measurements based on the particular data obtained. After a blood pressure measurement is determined at step 514, process 500 may return to step 502 and detect a new PPG signal (or access a new segment of a running PPG signal). As such, process 500 may generate blood pressure measurements continuously, with appropriate recalibrations as needed, based at least in part on the determinations in steps 504 and 506.

After blood pressure measurements are determined, the measurements may be outputted, stored, or displayed in any suitable fashion. For example, multi-parameter patient monitor 26 (FIG. 1) may display a patient's blood pressure on display 28 (FIG. 1). Additionally or alternatively, the measurements may be saved to memory or a storage device (e.g., ROM 52 or RAM 54 of monitor 14 (FIG. 2)) for later analysis or as a log of a patient's medical history.

In practice, one or more steps shown in process 500 may be combined with other steps, performed in any suitable order, performed in parallel (e.g., simultaneously or substantially simultaneously), or removed. For example, although method 500 has been illustrated in an iterative fashion, it will be understood that the arrival of a direct or indirect recalibration event may trigger substantially instantaneous recalibration, even if process 500 has not yet reached step 504 or step 506.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for monitoring blood pressure, the method comprising:
   receiving at a blood pressure monitoring system, from a hospital information system, data corresponding to a patient that is not determined based on a measured physiological parameter of the patient, wherein the data identifies a drug administration event;
   determining, based on the received data and an expected effect of the drug administration event on the patient's arterial compliance, whether a blood pressure monitoring system needs to be recalibrated;
   recalibrating the blood pressure monitoring system if it is determined that the blood pressure monitoring system needs to be recalibrated; and
   computing at least one blood pressure measurement of the patient using the recalibrated blood pressure monitoring system.

2. The method of claim 1 wherein receiving the data corresponding to the patient further comprises receiving data selected from the group consisting of: medical procedure data and medical equipment data.

3. The method of claim 1 further comprising:
   determining an identifier corresponding to a drug to be administered to the patient based at least in part on a scan of a tag corresponding to the drug; and
   storing the identifier in the hospital information system as part of the data corresponding to the patient.

4. The method of claim 1 wherein computing the at least one blood pressure measurement comprises:
   detecting a first photoplethysmograph (PPG) signal;
   detecting a second PPG signal;
   measuring a time difference between the first and second PPG signals; and
   generating the at least one blood pressure measurement based at least in part on the measured time difference.

5. The method of claim 4 wherein determining whether the blood pressure monitoring system needs to be recalibrated is further based at least in part on an item selected from the group comprising: the computed at least one blood pressure measurement and at least one characteristic of the first and second PPG signals.

6. The method of claim 1 wherein determining whether the blood pressure monitoring system needs to be recalibrated comprises scheduling a recalibration in response to determining that the blood pressure monitoring system needs to be recalibrated.

7. The method of claim 6 wherein:
   the data received from the hospital information system is indicative of a drug to be administered to the patient; and
   scheduling the recalibration is based at least in part on at least one characteristic of the drug to be administered.

8. The method of claim 1 wherein recalibrating the blood pressure monitoring system comprises:
   accessing a reference blood pressure measurement; and
   computing at least one mathematical constant based on the accessed reference blood pressure measurement, wherein computing the at least one blood pressure measurement is based at least in part on the computed at least one mathematical constant.

9. The method of claim 1 wherein the data that identifies the drug administration event comprises at least one of: drug identity data, actual or expected drug administration time data, drug dosage data, and method of drug delivery data.

10. The method of claim 1 wherein the data that identifies the drug administration event comprises actual or expected drug administration time.

11. A monitoring system comprising:
    a hospital information system operable to store data corresponding to a patient; and
    a blood pressure monitoring system coupled to a hospital information system, comprising a processor, operable to:
       receive the data from the hospital information system that is not determined based on a measured physiological parameter of the patient, wherein the data identifies a drug administration event;
       determine, based on the received data and an expected effect of the drug administration event on the patient's arterial compliance, whether the blood pressure monitoring system needs to be recalibrated;
       recalibrate the blood pressure monitoring system if it is determined that the blood pressure monitoring system needs to be recalibrated; and
       compute at least one blood pressure measurement of the patient using the recalibrated blood pressure monitoring system.

12. The monitoring system of claim 11 wherein the hospital information system is further operable to receive data selected from the group consisting of: medical procedure data and medical equipment data.

13. The monitoring system of claim 11 wherein the hospital information system is further operable to:
    determine an identifier corresponding to a drug to be administered to the patient based at least in part on a scan of a tag corresponding to the drug; and
    store the identifier as part of the data corresponding to the patient.

14. The monitoring system of claim 11 further comprising:
    a first sensor operable to detect a first photoplethysmograph (PPG) signal; and a second sensor operable to detect a second PPG signal, wherein the blood pressure monitoring system is further operable to:
  measure a time difference between the first and second PPG signals; and
  generate the at least one blood pressure measurement based at least in part on the measured time difference.

15. The monitoring system of claim 14 wherein the blood pressure monitoring system is further operable to determine whether the blood pressure monitoring system needs to be recalibrated based at least in part on an item selected from the group comprising: the computed at least one blood pressure measurement and at least one characteristic of the first and second PPG signals.

16. The monitoring system of claim 11 wherein the blood pressure monitoring system is further operable to schedule a recalibration in response to determining that the blood pressure monitoring system needs to be recalibrated.

17. The monitoring system of claim 16 wherein:
  the hospital information system is further operable to store data indicative of a drug to be administered to the patient; and
  the blood pressure monitoring system is further operable to schedule the recalibration based at least in part on at least one characteristic of the drug to be administered.

18. The monitoring system of claim 11 wherein the blood pressure monitoring system is further operable to:
  access a reference blood pressure measurement;
  compute at least one mathematical constant based on the accessed reference blood pressure measurement; and
  compute the at least one blood pressure measurement based at least in on the at least one mathematical constant.

19. A non-transitory computer-readable medium for use in determining blood pressure, the non-transitory computer-readable medium having computer program instructions recorded thereon, wherein the computer program instructions, when executed by a blood pressure monitoring system comprising a processor, cause the blood pressure monitoring system to:
  receive, from a hospital information system, data corresponding to a patient that is not determined based on a measured physiological parameter of the patient, wherein the data identifies a drug administration event;
  determine, based on the received data and an expected effect of the drug administration event on the patient's arterial compliance, whether the blood pressure monitoring system needs to be recalibrated;
  recalibrate the blood pressure monitoring system if it is determined that the blood pressure monitoring system needs to be recalibrated; and
  compute at least one blood pressure measurement of the patient using the recalibrated blood pressure monitoring system.

20. The non-transitory computer-readable medium of claim 19, wherein the received data is further selected from the group consisting of: medical procedure data and medical equipment data.

21. The non-transitory computer-readable medium of claim 19, wherein the computer program instructions, when executed on the blood pressure monitoring system, further cause the blood pressure monitoring system to schedule a recalibration that is determined to be necessary.

22. The non-transitory computer-readable medium of claim 21, wherein the computer program instructions, when executed on the blood pressure monitoring system, further cause the blood pressure monitoring system to:
  receive from the hospital information system data indicative of a drug to be administered to the patient; and
  schedule the recalibration based at least in part on at least one characteristic of the drug to be administered.

* * * * *